US008992417B2

(12) United States Patent
Belafsky et al.

(10) Patent No.: US 8,992,417 B2
(45) Date of Patent: Mar. 31, 2015

(54) FEEDING TUBE SYSTEM

(75) Inventors: Peter C. Belafsky, Davis, CA (US);
Robert J. Stinauer, Valencia, CA (US)

(73) Assignee: The Regents of the University of California, Oakland, CA (US)

( * ) Notice: Subject to any disclaimer, the term of this patent is extended or adjusted under 35 U.S.C. 154(b) by 613 days.

(21) Appl. No.: 12/920,084

(22) PCT Filed: Feb. 27, 2009

(86) PCT No.: PCT/US2009/035460
§ 371 (c)(1),
(2), (4) Date: Nov. 24, 2010

(87) PCT Pub. No.: WO2009/108854
PCT Pub. Date: Sep. 3, 2009

(65) Prior Publication Data
US 2011/0060187 A1 Mar. 10, 2011

Related U.S. Application Data

(60) Provisional application No. 61/032,001, filed on Feb. 27, 2008.

(51) Int. Cl.
*A61B 1/00* (2006.01)
*A61J 15/00* (2006.01)
*A61B 1/04* (2006.01)

(52) U.S. Cl.
CPC .......... *A61J 15/0003* (2013.01); *A61J 2205/00* (2013.01); *A61J 15/0061* (2013.01); *A61J 15/0007* (2013.01)

USPC ............ 600/104; 600/114; 600/129; 600/153

(58) Field of Classification Search
USPC .......... 600/101, 102, 114, 127, 129, 153, 104
See application file for complete search history.

(56) References Cited

U.S. PATENT DOCUMENTS

| 4,182,342 A | 1/1980 | Smith |
| 4,249,535 A | 2/1981 | Hargest, III |
| 4,384,584 A | 5/1983 | Chen |
| 4,410,320 A | 10/1983 | Dykstra et al. |
| 4,634,425 A | 1/1987 | Meer |

(Continued)

FOREIGN PATENT DOCUMENTS

| JP | 2006-87687 A | 6/2004 |
| JP | 2006-314802 A | 11/2006 |

(Continued)

OTHER PUBLICATIONS

Mitchell, et al., "Transnasal Endoscopic Technique for Feeding Tube Placement," 1992, Gastrointestinal Endoscopy, vol. 38, No. 5, 596-597.

(Continued)

*Primary Examiner* — Alireza Nia
(74) *Attorney, Agent, or Firm* — Kilpatrick Townsend & Stockton LLP

(57) ABSTRACT

An endoscope collar for use with an endoscope. The endoscope collar comprising a main portion comprising a proximal end that detachably couples to an end of the endoscope and a collar protrusion extending from the main portion. The collar protrusion is configured to be removably located within the aperture of a tube (e.g., a feeding tube).

5 Claims, 6 Drawing Sheets

(56) References Cited

U.S. PATENT DOCUMENTS

| | | |
|---|---|---|
| 4,672,960 A | 6/1987 | Frankel |
| 4,704,111 A | 11/1987 | Moss |
| 4,778,448 A | 10/1988 | Meer |
| 4,790,832 A | 12/1988 | Lopez |
| 4,828,550 A | 5/1989 | Kurimoto |
| 4,874,365 A | 10/1989 | Frederick et al. |
| 4,881,810 A * | 11/1989 | Hasegawa .................. 356/241.5 |
| 4,895,562 A | 1/1990 | Lopez |
| 5,085,216 A | 2/1992 | Henley, Jr. et al. |
| 5,167,220 A | 12/1992 | Brown |
| 5,322,513 A | 6/1994 | Walker |
| 5,334,167 A | 8/1994 | Cocanower |
| 5,554,140 A | 9/1996 | Michels et al. |
| 5,665,052 A | 9/1997 | Bullard |
| 5,846,181 A | 12/1998 | Heckele et al. |
| 6,322,495 B1 | 11/2001 | Snow et al. |
| 6,506,150 B1 | 1/2003 | Ouchi |
| 6,712,757 B2 | 3/2004 | Becker et al. |
| 6,878,106 B1 | 4/2005 | Herrmann |
| 6,997,931 B2 | 2/2006 | Sauer et al. |
| 7,081,097 B2 | 7/2006 | Martone |
| 7,566,300 B2 | 7/2009 | Devierre |
| 7,575,548 B2 * | 8/2009 | Takemoto et al. ............ 600/104 |
| 7,670,282 B2 | 3/2010 | Mathis |
| 2001/0000040 A1 | 3/2001 | Adams |
| 2002/0107530 A1 | 8/2002 | Sauer |
| 2002/0183591 A1 | 12/2002 | Matsuura |
| 2003/0036679 A1 | 2/2003 | Kortenbach et al. |
| 2003/0135091 A1 | 7/2003 | Nakazawa et al. |
| 2003/0195387 A1 | 10/2003 | Kortenbach |
| 2004/0064017 A1 | 4/2004 | Cappiello |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2006/0069304 A1 | 3/2006 | Takemoto |
| 2006/0258907 A1 | 11/2006 | Stefanchik et al. |
| 2006/0259010 A1 | 11/2006 | Stefanchik et al. |
| 2006/0281970 A1 | 12/2006 | Stokes et al. |
| 2007/0203393 A1 | 8/2007 | Stefanchik |
| 2008/0103357 A1 * | 5/2008 | Zeiner et al. .................. 600/104 |

FOREIGN PATENT DOCUMENTS

| | | |
|---|---|---|
| JP | 2007296323 A | 11/2007 |
| WO | 2007/135665 A2 | 11/2007 |

OTHER PUBLICATIONS

Pleatman et al., "Endoscopic Placement of Feeding Tubes in the Critically Ill Patient," Jul. 1987, Surgery, Gynecology & Obstetrics, vol. 165, 69-70.

Stark et al., "Endoscopically Place Nasoenteral Feeding Tubes: Indications and Techniques." Apr. 1991, The American Surgeon, vol. 57, No. 4, 203-205.

International Search Report from PCT/US09/35460, mailed Jul. 17, 2009 (3 pages).

Written Opinion of the International Searching Authority from PCT/US09/35460, mailed Jul. 17, 2009 (9 pages).

Office Action of Dec. 30, 2009 in related U.S. Appl. No. 11/795,398.

International Search Report from PCT/US06/01877, mailed Sep. 24, 2007 (3 pages) in related U.S. Appl. No. 11/795,398.

Written Opinion of the International Searching Authority from PCT/US06/01877, mailed Sep. 24, 2007 (7 pages) in related U.S. Appl. No. 11/795,398.

Notice of Allowance of Aug. 19, 2010 in related U.S. Appl. No. 11/795,398.

Japanese Office Action mailed Jun. 14, 2013 in JP Application No. 2010-548900, with translation.

Office Action mailed Jun. 24, 2014, from corresponding Japanese Application No. 2010/548900 (5 pages).

Extended European Search Report mailed Nov. 12, 2014, from European Application No. 09715303.5 (8 pages).

* cited by examiner

FEEDING TUBE SYSTEM

CROSS-REFERENCES TO RELATED APPLICATIONS

This application is the U.S. National Stage entry of International Application No. PCT/US09/035,460, International filing date of Feb. 27, 2009, which claims the benefit of U.S. Provisional Patent Application No. 61/032,001 entitled "Feeding Tube System" filed on Feb. 27, 2008. The entire contents of these applications are herein incorporated by reference for all purposes.

BACKGROUND

Clinicians who want to place nasal or oral enteral feeding tubes in their patients currently rely one of three methods. One method involves blindly passing the feeding tube into the stomach and relying upon gravity and peristalsis to carry it from the stomach into the jejunum. Another method uses fluoroscopy to pass the feeding tube under radiologic guidance. Finally, per-oral sedated endoscopy may be employed to guide a blindly passed transnasal tube from the stomach into the jejunum.

Each of the above-noted procedures is undesirable for a variety of reasons. For example, the blind placement of a feeding tube into a patient can result in the inadvertent intubation of the trachea and possible bronchopleural injuries. Fluoroscopic placement methods are complicated and require the assistance of a radiology department. Sedation is not desirable and poses an inherent risk.

SUMMARY OF THE INVENTION

Embodiments of the invention are directed to apparatuses and methods that can be used to insert a tube (e.g., a feeding tube) into a patient. The apparatuses and methods are desirably used without sedation and without fluoroscopy.

One embodiment is directed to an endoscope collar for use with an endoscope. The endoscope collar comprising a main portion comprising a proximal end that detachably couples to an end of the endoscope and a collar protrusion extending from the main portion. The collar protrusion is configured to be removably located within the aperture of a tube (e.g., a feeding tube).

Another embodiment is directed to a placement tube system comprising a tube, a stylet slidably located within the tube, and an endoscope collar that removably couples to a distal end of an endoscope. The endoscope collar has a collar protrusion capable of being removably located within an aperture of the tube. The collar protrusion detachably couples to the stylet within the tube. The endoscope collar holds the endoscope and the tube substantially in longitudinal alignment during placement of the tube.

Another embodiment is directed to a method of placing a tube comprising inserting a portion of a tube system into a patient. The tube system includes a tube, a stylet slidably located within the tube, an endoscope, and an endoscope collar removably coupled to a distal end of an endoscope. The method also includes endoscopically placing the tube in the patient wherein the endoscope and the tube are held substantially in longitudinal alignment by the endoscope collar while placing the tube. The method further includes removing the endoscope and the endoscope collar from the patient and removing the stylet from the patient, while leaving the tube in place.

These and other embodiments of the invention are described in detail below.

DETAILED DESCRIPTION

Embodiments of the invention are directed to endoscope collars, feeding tube placement systems having endoscope collars, and methods of using feeding tube placement systems with endoscope collars.

Various embodiments of the invention provide a number of technical advantages. One technical advantage is that the endoscope collar does not require tightening around the endoscope, which reduces the risk of damaging the endoscope. Another technical advantage is that using a feeding tube placement system with an endoscope collar improves patient safety. Positioning the feeding tube using this feeding tube placement system is a relatively simple and quick procedure, which can reduce stress on the patient and improve patient safety. In addition, the endoscope collar restricts relative movement between it and the feeding tube to keep the feeding tube aligned with the endoscope during placement of the feeding tube. Keeping the endoscope and feeding tube aligned can prevent misplacement of the feeding tube and improve patient safety. Furthermore, the endoscope collar is removed from the patient with the endoscope which can avoid potential damage from being inadvertently left inside the patient.

Certain embodiments of the invention may include none, some, or all of the above technical advantages. One or more other technical advantages may be readily apparent to one skilled in the art from the figures, descriptions, and claims included herein.

Figure 1:
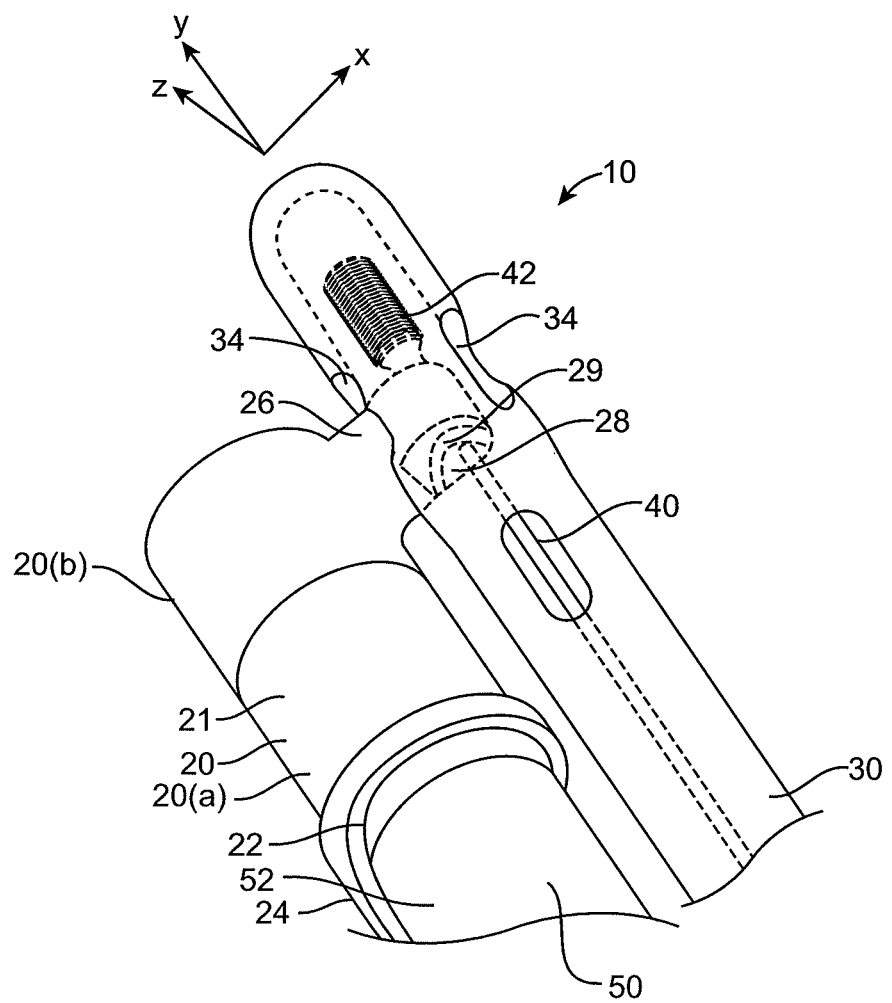
FIG. 1 is a drawing of a perspective view of components of a feeding tube placement system including an endoscope collar, a feeding tube, a stylet, and an endoscope, according to an embodiment of the invention.

FIG. 1 is a drawing of a perspective view of components of a feeding tube placement system 10 including an endoscope collar 20 having a proximal end 20(a) and a distal end 20(b), a feeding tube 30, a stylet 40, and an endoscope 50, according to an embodiment of the invention. The endoscope collar 20 includes a main tubular portion 21 having an inner surface 22 that couples to the endoscope 50. The endoscope collar 20 includes a flap 24 at the proximal end 20(a) and a collar protrusion 26 extending radially away from the distal end 20(b) of the endoscope collar 20. The feeding tube 30 has a feeding tube aperture 34 for slidably receiving the collar protrusion 26 into the feeding tube 30. The stylet 40 is slidably located within the feeding tube 30 and includes a stylet spring 42. The stylet 40 with its stylet spring 42 is inserted through the aperture 29 into the passageway 28 to secure the endoscope collar 20 to the feeding tube 30. The endoscope 50 has a distal end 52 that fits into the proximal end 20(a) of the endoscope collar 20 and secures the endoscope 50 to the endoscope collar 20 so that the endoscope 50 and the feeding tube 30 are placed substantially in a side-by-side relationship.

In operation, a portion of the collar protrusion 26 is inserted into the feeding tube aperture 34. The stylet 40 and the stylet spring 42 are fed through the feeding tube 30 and through the passageway 28 in the collar protrusion 26 to secure the endoscope collar 20 to the feeding tube 30. The endoscope 50 is then secured to the proximal end 20(a) of the endoscope collar 20 to complete the feeding tube placement system 10. Once assembled, a user introduces the feeding tube placement system 10 into a patient and endoscopically places the feeding tube at the stomach, jejunum, or other internal body structure of the patient 30 using the guide wire of the stylet 40. Once the feeding tube 30 is in place, the user pulls the stylet spring 42 through the passageway 28 in the collar protrusion 26 to release the endoscope collar 20 from the feeding tube 30. The user can then remove from the patient the endoscope collar 20 and the endoscope 50 by pulling the endoscope 50. The stylet 40 can then be pulled out of the feeding tube 30 and removed from the patient, which completes the placement of the feeding tube 30.

The endoscope collar 20 refers to any suitable device that can secure (and release) the endoscope 50 to the feeding tube 30 in a side-by side relationship and substantially maintain the alignment of the endoscope 50 and the feeding tube 30 while the feeding tube 30 is being placed in the patient. The endoscope collar 20 can be made of any suitable shape, made using any suitable number of components, and made of any suitable material (e.g., rubber, plastic, etc.). In one embodiment, the endoscope collar 20 may be formed of a single-piece molded plastic or other suitable material. In another embodiment, the endoscope collar 20 may be comprised of multiple components that are fixed together so that the movement of one component will cause the movement of the other components.

The endoscope collar 20 includes a main tubular portion 21 having an inner surface 22. The distal end 52 of the endoscope 50 fits within the main tubular portion 20 at the proximal end 20(a) of the endoscope collar 20. The inner surface 22 may be a mating surface with the same curvature as the outside surface of the distal end 52 of the endoscope 50. In one example, the inner surface 22 is cylindrical. The inner surface 22 may also include a mechanism suitable for securing the endoscope collar 20 to the endoscope 50. For example, the inner surface 22 may be sized to create an interference fit connection with the distal end 52 of the endoscope 50 by having the diameter of the inner surface 22 be less than the outer diameter of the distal end 52. As another example, the inner surface 22 may have a set of threads that engage with another set of mating threads on the distal end 52 of the endoscope 50. The main tubular portion 21 may also have a structure (e.g., a stop) coupled to the inner surface 22 that may stop the endoscope 50.

Although not shown, the endoscope collar 20 also includes a structure at the distal end 20(b) that allows the endoscope 50 to view through the distal end 20(b) of the endoscope collar 20 when the endoscope 50 is located within the endoscope collar 20. The structure may be a transparent layer or may be an opening of any suitable shape that can allow visibility by the endoscope 50. In an exemplary embodiment, the structure is a transparent glass or plastic layer at the distal end 20(b). The structure may protect the endoscope 50 from being contacted and potentially damaged during placement of the feeding tube 30.

The endoscope collar 20 also includes an axially extending flap 24 at the proximal end 20(a). The flap 24 refers to any suitable structure that helps a user guide the endoscope 50 into the main tubular portion 21 and/or helps the user remove the endoscope 50 from the endoscope collar 20. In the illustrated example, the flap 24 is an integral portion of the endoscope collar 20. The flap 24 has an inner surface with a diameter that is approximately the same as the outer diameter of the endoscope 50. In one embodiment, the user may guide the endoscope 50 into the main tubular portion 21 of the endoscope collar 20 by contacting the distal end 52 of the endoscope 50 to the inside surface of the flap 24 and allow the endoscope 50 to slide along a portion of the inside surface of the flap 24 until the endoscope 50 can be secured in place in the endoscope collar 20. In another embodiment, the user may pull the flap 24 outward to detach the endoscope 50 from the endoscope collar 20.

The endoscope collar 20 also includes a collar protrusion 26 that extends radially away from the main tubular portion 21. Although the collar protrusion 26 is shown to be located on a side of the distal end 20(b) of the endoscope collar 20, it may be at other locations of the endoscope collar 20 in other embodiments. For example, the collar protrusion 26 could be located at the proximal end 20(a). In the illustrated example, the collar protrusion 26 is an integral part of the endoscope collar 20. In other embodiments, the collar protrusion may be a separate part that is fixed to the main tubular portion 21.

The collar protrusion 26 can include any suitable structure(s) for coupling the main tubular portion 21 of the endoscope collar 20 to the feeding tube 30 and maintaining the distal ends of the endoscope collar 20 and the feeding tube 30 in longitudinal alignment during placement of the feeding tube 30. In longitudinal alignment, the centerline of the endoscope collar 20 at its distal end 20(b) remains substantially parallel to the centerline axis of the feeding tube 30 at its distal end. These alignment structures may substantially restrict the relative translational and rotational movement between the feeding tube 30 and the endoscope collar 20 and an attached endoscope 50.

The collar protrusion 26 forms a passageway 28 for receiving the stylet spring 42 and the guide wire of the stylet 40. The endoscope collar 20 and the feeding tube 30 are coupled together once the stylet spring 42 is pushed through the passageway 28. This coupling can substantially maintain the feeding tube 30 at a particular distance from the endoscope 50 (and endoscope collar 20). This distance between the endoscope 50 and the feeding tube 30 is based on the length of the collar protrusion 26, the diameter of the passageway, and the diameter of the feeding tube 30. This coupling can substantially restrict the relative translation between the feeding tube 30 and the endoscope 50 in the x-axis and z-axis and substantially restrict the relative rotation in the x-axis and z-axis. The passageway 28 may be generally cylindrical in shape and can be of any suitable size for allowing passage of the stylet 40 and the stylet spring 42.

The collar protrusion 26 can fit into one of the feeding tube apertures 34 at the side of the feeding tube 30. The collar protrusion 26 may be placed into one of the feeding tube apertures 34 to allow the placement of the stylet spring 42 and the guide wire of the stylet 40 through the passageway 28.

Once the stylet spring 42 is pushed through the passageway 28, the endoscope collar 20 and the feeding tube 30 are coupled together.

When the collar protrusion 26 is located inside the feeding tube aperture 34, it is blocked from movement in the y-axis by the edges of the feeding tube aperture 34. In some embodiments, the feeding tube aperture 34 and the width of the collar protrusion 26 are sized to substantially restrict the relative translational movement between the endoscope 50 and the feeding tube 30 along the y-axis. For example, the width of the collar protrusion 26 can be sized to be slightly less (e.g., 0.5 mm) than the length of the feeding tube aperture 34 in the direction of the y-axis.

The feeding tube 30 refers to any suitable tubing (e.g., a French tube) that can be used to provide nutrition to the patient. The feeding tube 30 may have any number of apertures. In the illustrated embodiment, the feeding tube 30 includes two feeding tube apertures 28 on opposing sides of the distal end of the feeding tube 30. At least one of the feeding tube apertures 28 is of a suitable size and shape to receive the collar protrusion 26 and allow the collar protrusion 26 to be removed from the feeding tube aperture 28 when the feeding tube placement system 10 is located in the patient. Although feeding tubes 30 are discussed in detail in some embodiments, other types of tubes such as air tubes can be used in other embodiments. The feeding tube 30 can be made of any suitable material. For example, the feeding tube 30 can be made of medical grade silicone rubber. The feeding tube 30 may have any suitable dimensions. In an exemplary embodiment, the feeding tube 30 may have dimensions that allow the feeding tube 30 to be inserted into a nasal or oral cavity of a patient.

The stylet 40 refers to any suitable device that can be used to guide the feeding tube placement system 10 through the patient and that can be used to secure the feeding tube 30 to the collar protrusion 26 of the endoscope collar 20 and release the feeding tube 30 from the collar protrusion 26. The stylet 40 can be made of any suitable material. For example, the stylet 40 can be made of 317 passivated stainless steel.

The stylet 40 includes a guide wire and a stylet spring 42 attached to the distal end of the guide wire. The guide wire may be used to stiffen the feeding tube 40 as it is being inserted into the patient. When the feeding tube 30 and endoscope 50 are coupled together, the user can manipulate the guide wire to locate the feeding tube and the endoscope 50. The guide wire of the stylet 40 can be of any suitable size and material.

The stylet spring 42 can be any suitable device that can be pushed through the passageway 28 and couple the endoscope collar 20 to the feeding tube 30 and can be pulled through the passageway 28 to allow the stylet 40 to be uncoupled from the endoscope collar 20. In the illustrated example, the stylet spring 42 is a spring that tapers down at the attachment to the guide wire. In this example, the user can pull on the guide wire to stretch the stylet spring 42 and allow the stylet 40 to be pulled through the passageway 28 and decoupled from the endoscope protrusion 26. Once the stylet 42 is decoupled, the endoscope collar 20 can be removed from the feeding tube aperture 34 of the feeding tube 30. The feeding tube 30 can then be decoupled from the endoscope collar 20 and the endoscope 50, if attached. In one embodiment, pulling on the stylet spring 42 may break the stylet spring 24 which releases it. In this case, the stylet spring 24 may be made of a digestible material or other suitable material. The stylet spring 42 can be of any suitable size that allows the stylet spring 42 to pass through the feeding tube 30 and pass through the passageway 28 in the collar protrusion 26. In some cases, the stylet spring 42 may have a smaller diameter than a typical stylet spring.

The endoscope 50 refers to any suitable flexible endoscope having any suitable diameter. An exemplary embodiment of the endoscope 50 is an ultrathin flexible endoscope (e.g., a Pentax™ endoscope). The endoscope 50 has a distal end 52 that is inserted into the endoscope collar 20. In some embodiments, the distal end 52 may have threads on an outside surface that engage threads on the inside surface 22 of the endoscope collar 20. The endoscope 50 includes instrumentation (e.g., a light and camera) for capturing images within an endoscope viewing cone 60 (shown in FIG. 2) in front of the endoscope 50. The endoscope can have any suitable dimensions. In an exemplary embodiment, the endoscope 50 has dimensions that allow the endoscope 50 to be inserted into a patient.

Figure 2:
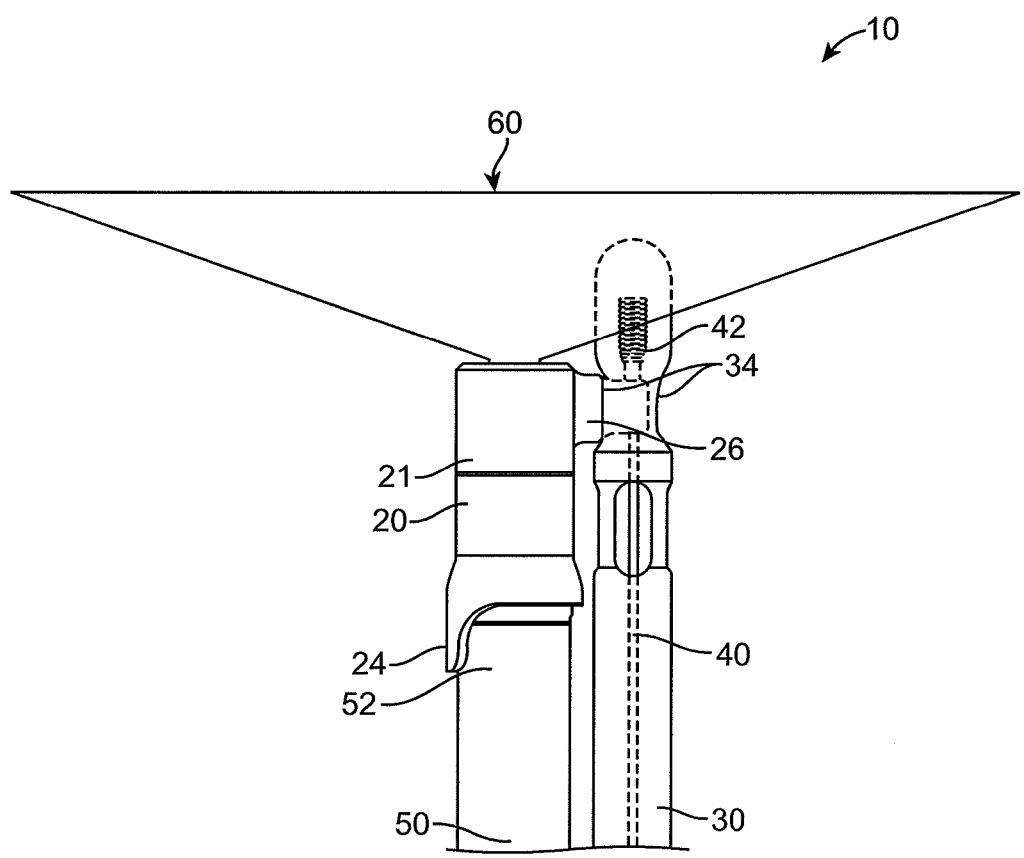
FIG. 2 is a drawing of a side view of components of a feeding tube placement system and an endoscope viewing cone, according to an embodiment of the invention.

FIG. 2 is a drawing of a side view of components of a feeding tube placement system 10 and an endoscope viewing cone 60, according to an embodiment of the invention. The feeding tube placement system 10 has an endoscope collar 20, a feeding tube 30, a stylet 40, and an endoscope 50. The endoscope collar 20 includes a main tubular portion 21 having a flap 24 and a collar protrusion 26. The feeding tube 30 includes two feeding tube apertures 34. The collar protrusion 26 is inserted into one of the feeding tube apertures 34 and into the feeding tube 30. The stylet 40 includes a stylet spring 42 that is inserted into the feeding tube 30 through passageway 28 to secure the endoscope collar 20 to the feeding tube 30. The endoscope 50 has a distal end 52 that fits into the proximal end 20(*a*) of the endoscope collar 20 and secures the endoscope 50 to the endoscope collar 20. In feeding tube placement system 10, endoscope 50 and feeding tube 30 are secured in side-by-side relationship.

The endoscope viewing cone 60 is a cone-shaped representation of the range of visibility of the endoscope 50. In the illustrated example, the endoscope viewing cone 60 includes the distal tip of the feeding tube 30 so that the tip is visible by the endoscope 50. The user can see the tip of the feeding tube 30 by viewing the images provided by the endoscope 50 during the placement procedure.

Figure 3:
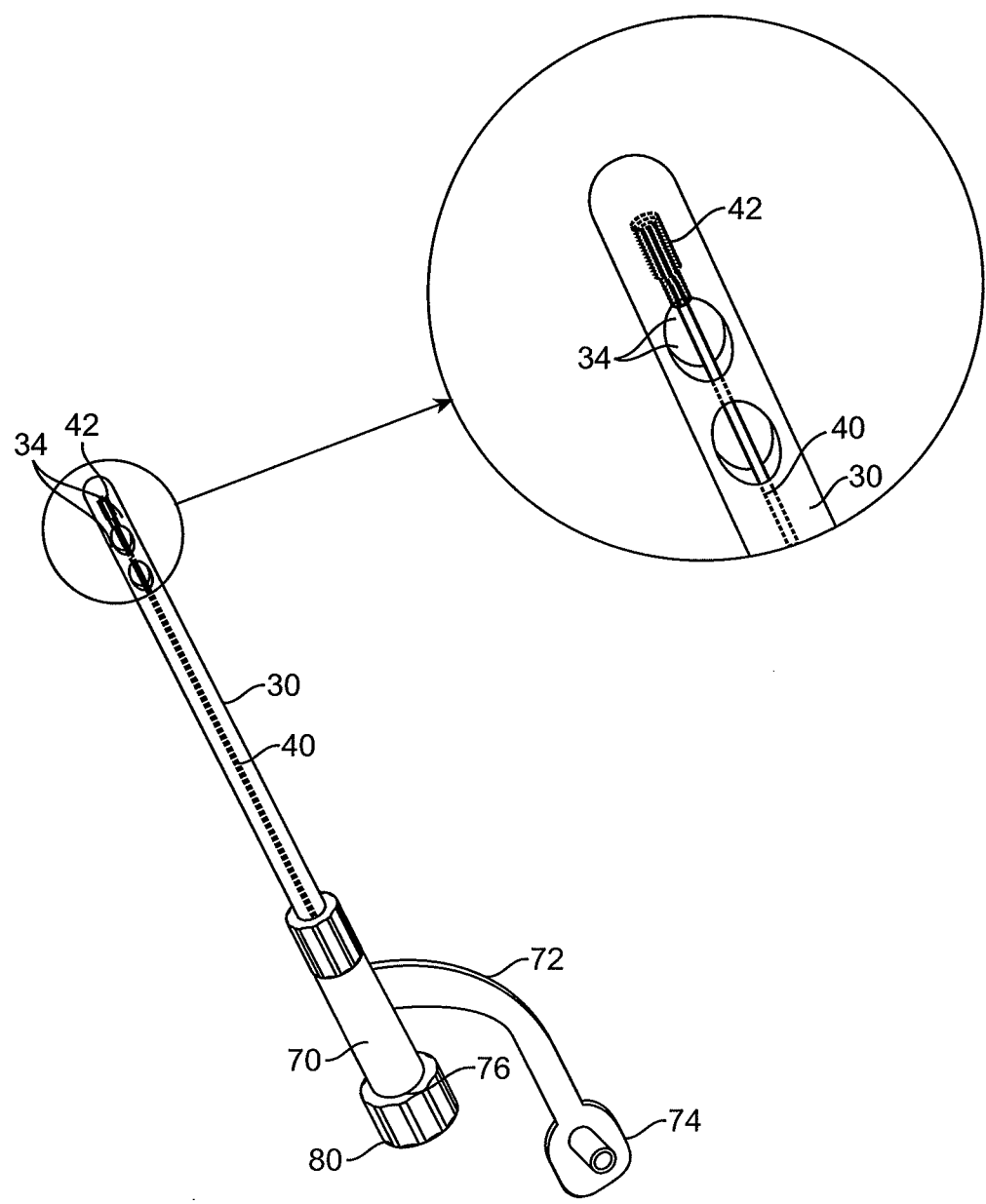
FIG. 3 is a drawing of a perspective view of components of a feeding tube placement system including a feeding tube, a stylet, a port, and a stylet cap, according to an embodiment of the invention.

FIG. 3 is a drawing of a perspective view of components of a feeding tube placement system 10 including a feeding tube 30, a stylet 40, a port 70, and a stylet cap 80, according to an embodiment of the invention. These components can be included in the feeding tube placement system 10 in some embodiments. The feeding tube 30 includes two feeding tube apertures 34. The stylet 40 is slidably located within the feeding tube 30. The stylet 40 includes a stylet spring 42. The port 70 comprises a port arm 72 communicating with a main portion of the port 70, a cap holder 74, and a port fitting 76 for engaging with the stylet cap 80.

The port 70 refers to any device suitable for sealing the interface between the proximal end of the feeding tube 30 and the stylet cap 80. The port 70 can be made of any suitable material that allows the stylet cap 80 to be firmly and easily connected to it. For example, the port 70 can be made of medical grade silicone rubber.

The port 70 comprises a port arm 72, a cap holder 74, and a port fitting 76. The cap holder 74 includes a protrusion for holding a cap such as a stylet cap 80. The port fitting 76 can be of any suitable shape and size to engage the stylet cap 80. The port fitting 76 can include any mechanism suitable for engaging the stylet cap 80. For example, the port fitting 76 may include threads on an outer surface that engage threads on an inner surface of the stylet cap 80.

The stylet cap 80 refers to any suitable device that can seal the port 70. The stylet cap 80 can be made of any suitable material (e.g., translucent/clear plastic). The stylet cap 80 can use any suitable mechanism for securely attaching to the port 70. For example, the stylet cap 80 may have an inner surface that is sized to form an interference fit with the outside surface of the port fitting 76 and/or the stylet cap 80 may have grooves on the inner surface that engage the outer surface of the port fitting 76.

Figure 4:
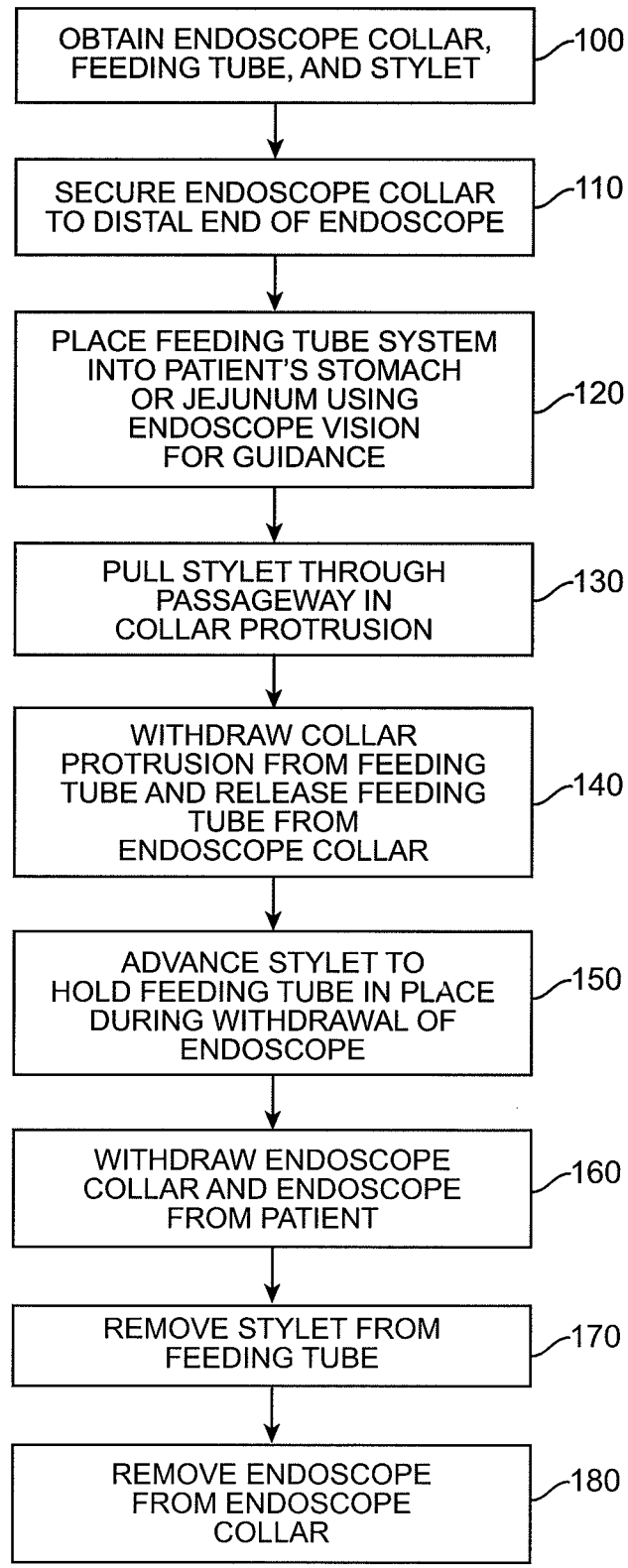
FIG. 4 is a flowchart describing a method of placing a feeding tube using a feeding tube placement system, according to embodiments of the invention.

FIG. 4 is a flowchart describing a method of placing a feeding tube 30 in a patient using a feeding tube placement system 10, according to embodiments of the invention. The user obtains the endoscope collar 20, the feeding tube 30, and the stylet 40 (step 100). In an exemplary embodiment, the endoscope collar 20, the feeding tube 30, and the stylet 40 are pre-assembled together and provided as an assembled package. The assembler of the package inserts a portion of the collar protrusion 26 of the endoscope collar 20 into the feeding tube aperture 34 and then slides the stylet 40 with the stylet spring 42 through the passageway 28 in the collar protrusion 26. Once the stylet spring 42 passes through the passageway 28, the feeding tube 30 is coupled to the endoscope collar 20. In other embodiments, the user obtains the endoscope collar 20, the feeding tube 30, and the stylet 40 and assembles the components.

The user then secures the distal end 52 of the endoscope 50 into the proximal end 20(a) of the endoscope collar 20 (step 110) to form the feeding tube placement system 10. In an exemplary embodiment, the endoscope collar 20 and the endoscope 50 are sized to form an interference fit to hold them together during placement of the feeding tube 30.

Once the feeding tube placement system 10 is assembled, the user manipulates the guide wire of the stylet 40 to guide the feeding tube placement system 10 into the patient's stomach or jejunum using the endoscope vision for guidance (step 120). In other embodiments, the user may place the feeding tube placement system 10 into other parts of the patient's body.

After the feeding tube 30 is in place, the user pulls on the guide wire to pull the stylet spring 42 through the passageway 28 in the endoscope protrusion 26 of the endoscope collar 20 (step 130). In some cases, the guide wire is pulled with a certain force or a certain distance to cause the stylet spring 42 to be released through the passageway 28. This force or distance may be required to break the stylet spring 42 or deform it to allow it to pass through the passageway 28. In one example, pulling on the guide wire a distance of 10 mm will release the stylet spring 42 from the passageway 28.

Once the stylet spring 42 is released through the passageway 28, the endoscope protrusion 26 can be withdrawn from the feeding tube 30, which releases the feeding tube 30 from the endoscope collar 20 (step 140). Once released, the feeding tube 30 and the endoscope collar 20 are uncoupled. In some cases, removing the stylet spring 42 from the passageway 28 also releases the endoscope protrusion 26 from the feeding tube 30.

To hold the feeding tube 30 in position while the endoscope 50 is being withdrawn, the user advances the stylet 40 into the feeding tube 30 (step 150). In some cases, the user may be required to advance the stylet 40 a certain distance such as 10 mm.

While holding the stylet 40 in place, the user withdraws the endoscope 50 and the attached endoscope collar 20 from the patient's body (step 160). The user removes the stylet 40 from the feeding tube 30 and out of the patient's body to complete the placement of the feeding tube 30 (step 170). After placing the feeding tube 30, the user removes the endoscope 50 from the endoscope collar 20 (step 180).

Figure 5:
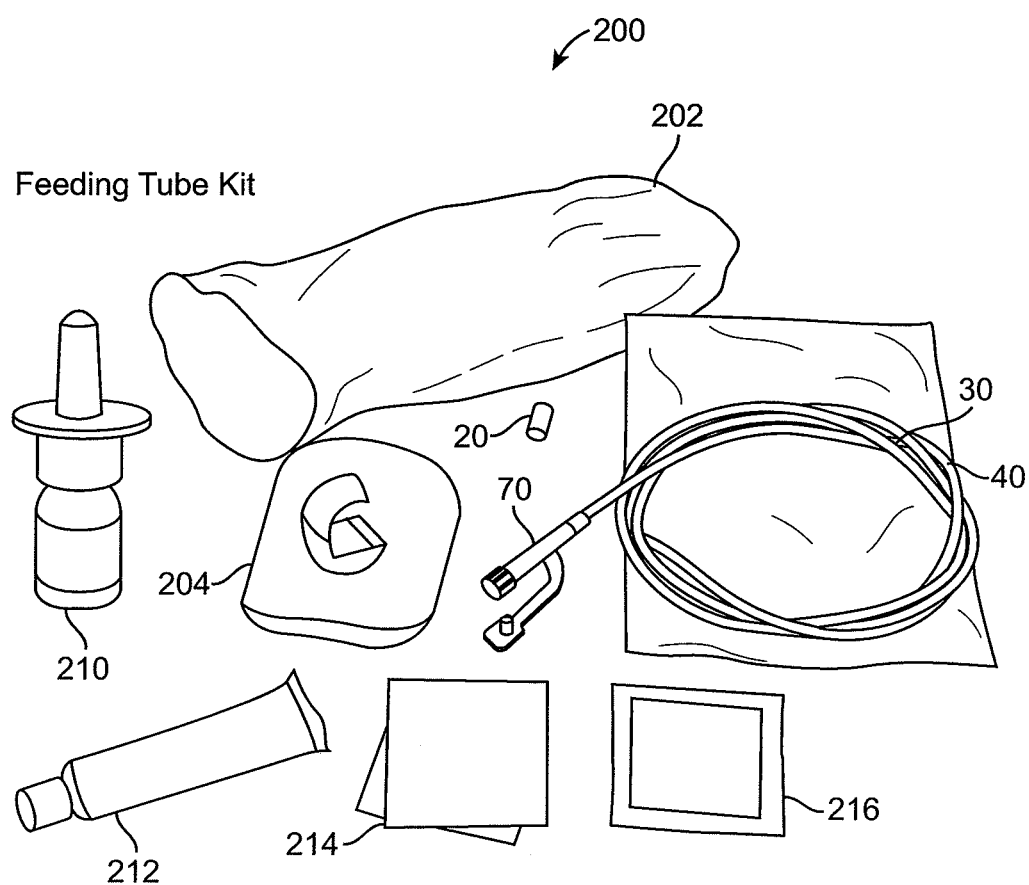
FIG. 5 is a photograph of a feeding tube kit, according to an embodiment of the invention.

FIG. 5 is a photograph of a feeding tube kit 200, according to an embodiment of the invention. The kit includes surgical gloves 202, a tube securing device 204, a port 70, a feeding tube 30 attached to the proximal end of the port 70, an endoscope collar 20, an anesthetic nasal spray 210, surgical lubricant 212, a skin protectant prep pad 214, and a protective barrier film 216. The feeding tube 30 includes a stylet 40 located therein. In other embodiments, the feeding tube kit 200 may include more, fewer, or other components. In some embodiments, the components of the feeding tube kit 200 can be placed into a container.

Figure 6A:
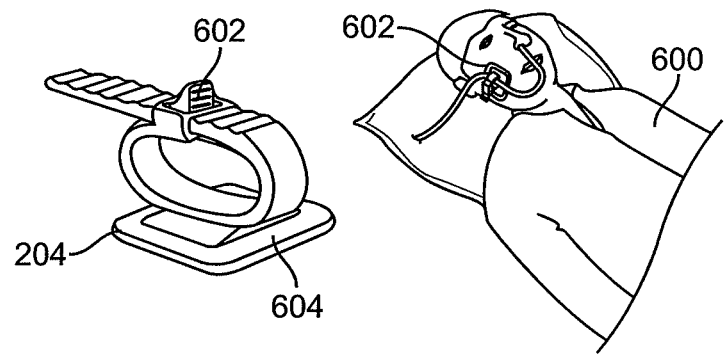
FIG. 6(a) is a drawing of a perspective view of a feeding tube that has been placed in a patient using the feeding tube placement system and a tube securing device, according to an embodiment of the invention.

FIG. 6(a) is a drawing of a perspective view of a feeding tube 30 that has been placed in a patient 600 using the feeding tube placement system 10 and a tube securing device 204, according to an embodiment of the invention. The tube securing device 204 includes an adhesive pad 60 coupled to a locking strap 604 which includes a thumb release 606.

After the feeding tube 30 has been placed, the user may secure a portion of the feeding tube 30 outside the body of the patient 600. Typically, the feeding tube 30 is secured to the patient's body close to the exit point from the patient 600 such as the patient's face, as shown in FIG. 6(a). To secure the feeding tube 30, the user can place the feeding tube 30 within the locking strap 604 and pull the locking strap 604 to couple the tube securing device 204 to the feeding tube 30. The user may then remove a liner on the adhesive pad 60 and places the adhesive pad 60 on the patient's body. To release the feeding tube 30 from the locking strap 604, the user can push the thumb release 606.

Figure 6B:
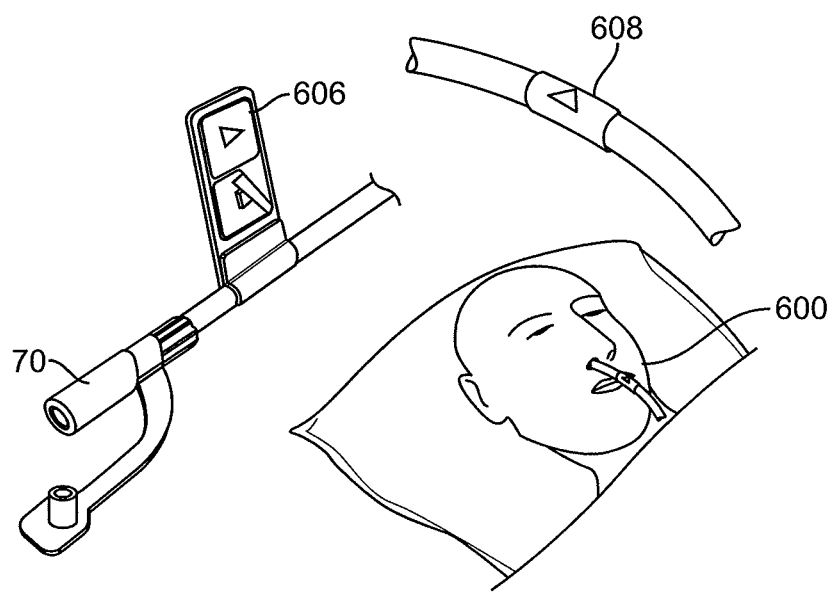
FIG. 6(b) is a drawing of a perspective view of a feeding tube that has been placed in a patient using the feeding tube placement system and a marking device, according to an embodiment of the invention.

FIG. 6(b) is a drawing of a perspective view of a feeding tube 30 that has been placed in a patient 600 using the feeding tube placement system 10 and a marking device 606, according to an embodiment of the invention. In the illustrated example, the marking device 606 is attached to the feeding tube proximal the port 70. In other embodiments, the marking device 606 can be located elsewhere. The marking device 606 can be any suitable device for placing a marking 608 on the feeding tube 30. The marking 608 can be at any location on the feeding tube 30. In the illustrated example, the marking 608 is placed proximate to the exit point of the feeding tube 30 from the patient 600.

Modifications, additions, or omissions may be made to the method without departing from the scope of the disclosure. The method may include more, fewer, or other steps. Additionally, steps may be performed in any suitable order without departing from the scope of the disclosure.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A placement tube system, comprising:
   a feeding tube;
   a stylet slidably located within the feeding tube having a lumen; and
   an endoscope collar that removably couples to a distal end of an endoscope, wherein the endoscope collar has a collar protrusion capable of being removably located within a feeding tube aperture that is in fluid communication with the lumen of the feeding tube, wherein the collar protrusion detachably couples to the stylet within the tube, wherein the endoscope collar holds the endoscope and the tube substantially in longitudinal alignment during placement of the tube, wherein the stylet includes a stylet spring, and wherein the collar protrusion comprises a passageway for receiving the stylet spring at a distal end of the stylet to detachably couple the stylet to the collar protrusion.

2. The placement tube system of claim 1, wherein a proximal end of the endoscope collar forms an interference fit with the endoscope.

3. The placement tube system of claim 1, further comprising a stylet cap removably coupled to a port coupled to the tube, the stylet cap having inner grooves that engage an outside surface of the port.

4. The placement tube system of claim 1, wherein the stylet and stylet spring are configured to be axially pulled in a proximal direction through the passageway of the protrusion to release the color protrusion.

5. The placement tube system of claim 4, wherein the stylet spring is configured to deform or break when axially pulled in a proximal direction through the passageway of the protrusion to release the color protrusion.

* * * * *